United States Patent [19]

Kabacoff et al.

[11] Patent Number: 4,510,250

[45] Date of Patent: Apr. 9, 1985

[54] METHOD OF HAIR DAMAGE ASSESSMENT

[75] Inventors: Bernard L. Kabacoff, Norwalk, Conn.; Alok K. Govil, Marlboro, N.J.

[73] Assignee: Revlon, Inc., New York, N.Y.

[21] Appl. No.: 528,919

[22] Filed: Sep. 2, 1983

[51] Int. Cl.³ .............................................. G01N 33/00
[52] U.S. Cl. ........................................ 436/63; 436/80
[58] Field of Search .................... 436/63, 2, 5, 80, 164

[56] References Cited

U.S. PATENT DOCUMENTS

| | | | |
|---|---|---|---|
| 3,748,096 | 7/1973 | Schmitt et al. | 436/80 |
| 3,895,001 | 7/1975 | Beck et al. | 526/308 X |
| 4,263,277 | 4/1981 | Tripathi et al. | 424/72 |
| 4,421,859 | 12/1983 | Boré et al. | 436/164 X |

Primary Examiner—Barry S. Richman
Assistant Examiner—Michael S. Gzybowski

[57] ABSTRACT

Described is a method for measuring hair damage by copper uptake using in the process a simple hair volume measuring device.

9 Claims, 9 Drawing Figures

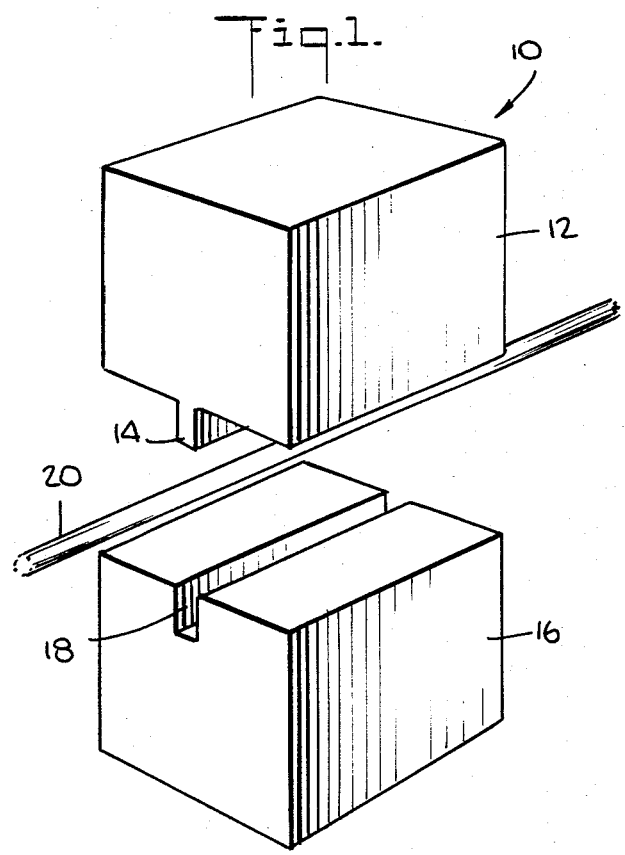
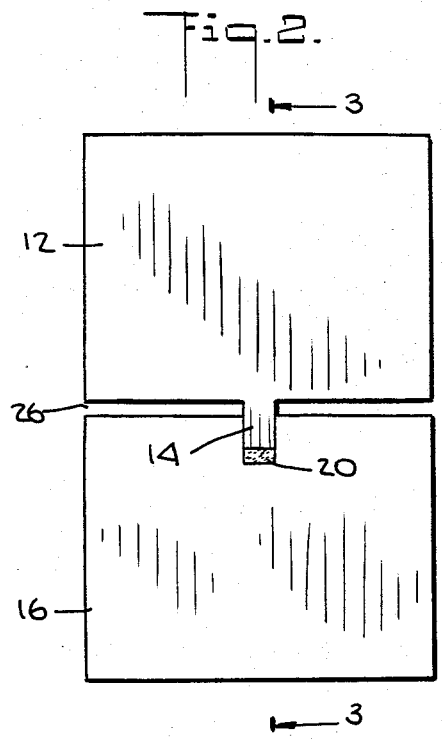
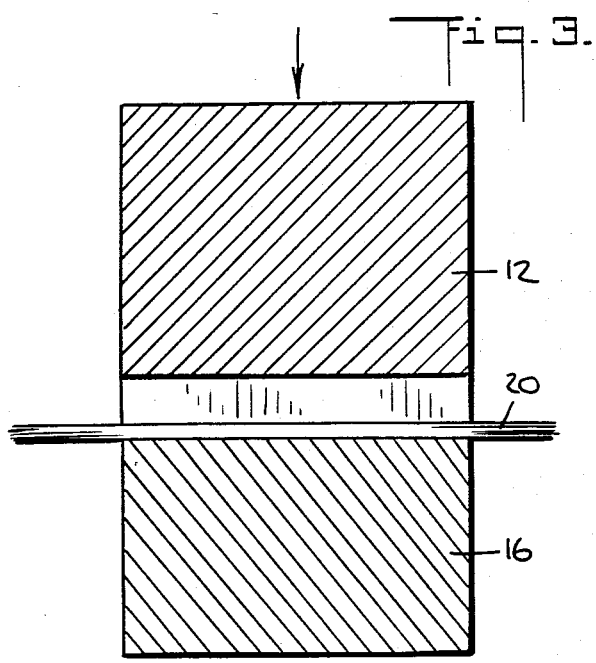
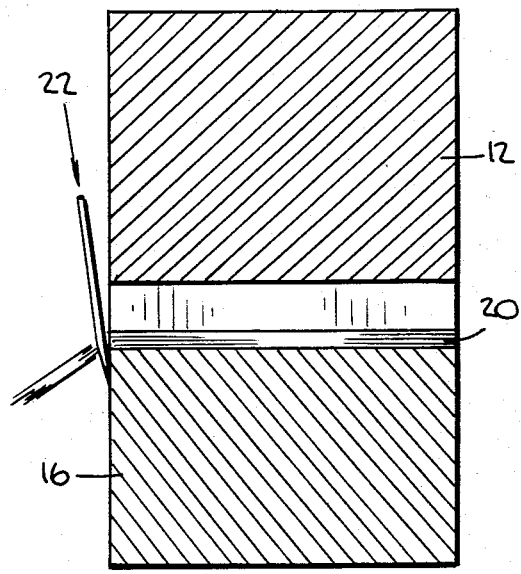
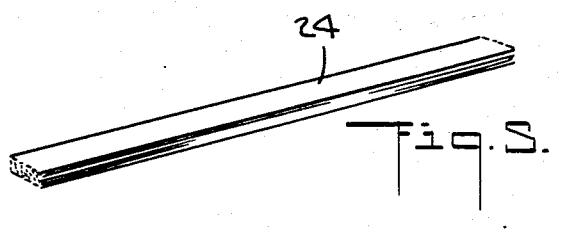

METHOD OF HAIR DAMAGE ASSESSMENT

BACKGROUND OF THE INVENTION

1. Field of the Invention

This invention relates to a method of assessing damage to human hair, and more particularly, to a method of quantifying human hair damage caused by hair treatment compositions applied thereto and damage caused to human hair by the environment.

2. Description of the Prior Art

Hair care is one of the most important parts of beauty care, and a large variety of hair treatment products are used for providing such care in the form of pre-shampoo conditioners, shampoos, after-shampoo conditioners, rinses, setting lotions, sprays, dyes, bleaches, permanent wave agents and the like. These products in addition to providing the desired result in the hair, such as luster, curl, combability, softness, color and an overall appealing look, also do damage to the hair, especially when used indiscriminantly without professional guidance. Damage to hair may also result from other sources, such as combing, humidity, dryness, dirt, sunrays, such as u.v. and infrared radiation, and pollution in the atmosphere. However, damage to hair occurs mostly in the form of physical and chemical changes in hair as a result of bleaching, oxidative dying, hair relaxing via alkaline relaxers and reducing waving and curling preparations.

Assessment of hair damage is desirable, so that corrective action may be taken. Such corrective action may be: the utilization of products which do not cause damage or their damaging affect is minimal; eliminating the use of deleterious products; using products in proper sequence to circumvent further damage; or using products designed to repair hair damage.

Measurement of hair damage is known in the prior art. For example, W. W. Edman and M. E. Marti, *Journal of the Society of Cosmetic Chemists*, pp: 133–145, September 1960, report a study on properties of peroxide-bleached hair and use as a measure of hair damage the so-called 20% index, which is the ratio of work required to stretch the fiber 20 percent after treatment with a peroxide bleach to the work required to stretch the fiber 20% before treatment. To measure the 20% index a constant Elongation Tester is used. The same study also shows measurement of hair damage by "extension-at-break" using a Scott Tester.

Measurement of hair damage via copper absorption is also known. U.S. Pat. No. 4,263,277 discloses a method for measuring hair damage by soaking a known weight of hair sample in a 0.1N tetraamine copper sulfate, followed by washing with water. The filtrate is then titrated against 0.1N sodium thiosulfate to determine the amount of copper absorbed by the hair. The damage to hair is assumed to correlate with the amount of copper absorbed by the hair sample.

While methods like these to assess hair damage are appropriate for investigational and research purposes, they are not suitable for use by hair-care professionals or for home use.

It is an object of the present invention to provide a method which can be easily applied by hair-care professionals as well as individuals to assess hair damage.

It is another object of the present invention to provide a simple device for measuring the volume of fibrous materials as well as measuring the volume of hair samples used in the method of assessing hair damage.

It is still another object of the present invention to provide stable copper solutions suitable for use in the method of assessing hair damage.

These and other objects are accomplished in accordance with the following description of the invention.

SUMMARY OF THE INVENTION

It has now been discovered that hair damage can be assessed by a simple, inexpensive method based on measuring the intensity of color of a copper complex solution subsequent to the reaction of the copper complex with a known amount of hair. The steps of hair damage assessment comprises:

(a) obtaining the weight of a hair sample;
(b) subjecting said sample to a copper solution to effect attachment of positively charged copper ions to negatively charged groups in the hair; and
(c) comparing color intensity of residual copper solution with color intensity of the copper solution prior to hair being subjected thereto.

The weight of a hair sample is obtained by measuring the volume of the hair sample using the hair volume measuring device of the present invention and converting the volume so obtained to weight by the use of a mathematical equation or a table calculated therefrom.

The hair volume measuring device comprises: a male member having a projection thereon; and a female member having a sample slot to receive and hold a sample as well as to engage said projection. Male and female members of the device are forced against each other compressing the hair sample placed in the sample slot. The width and length of the sample slot are known, and consequently the same dimensions of the sample are also known, while the height of the sample is obtained via measuring the distance between the surfaces of the male and female members of the device.

DETAILED DESCRIPTION OF THE INVENTION

Damage to hair caused by bleaching, oxidative dyeing, alkaline hair relaxers, reducing waving and curling preparations and the like results in the creation of negatively charged groups in the hair fiber. These groups readily react with the copper reagent. Thus, measurement of the amount of copper reacted with a known amount of hair is used to estimate the extent of hair damage.

Copper uptake by hair must be based on a known quantity of hair, such as weight. While in a research environment the weighing of a hair sample can be easily accomplished by the use of an analytical balance, in beauty salons or in the homes the weighing of such light materials as hair cannot be done simply and economically. One of the objects of the present invention is accomplished by the provision of a simple device by which quantitative measurements of a small hair sample can be easily made. The device is used to measure hair volume which is then converted to hair weight through the use of an equation or appropriate table.

HAIR VOLUME MEASURING DEVICE

BRIEF DESCRIPTION OF THE DRAWINGS

FIG. 1 is a perspective view of one embodiment of the hair volume measuring device of the present invention and includes a hair sample.

FIG. 2 is an end view of the device of FIG. 1.

FIG. 3 is a cross sectional view of FIG. 2 taken along lines 3—3.

FIG. 4 is the same cross sectional view as that shown in FIG. 3, but showing additionally the cutting off of that portion of the hair sample which extends out from the device.

FIG. 5 is a perspective view of the hair sample cut in FIG. 4.

DETAILED DESCRIPTION OF THE DRAWINGS

Figure 6:
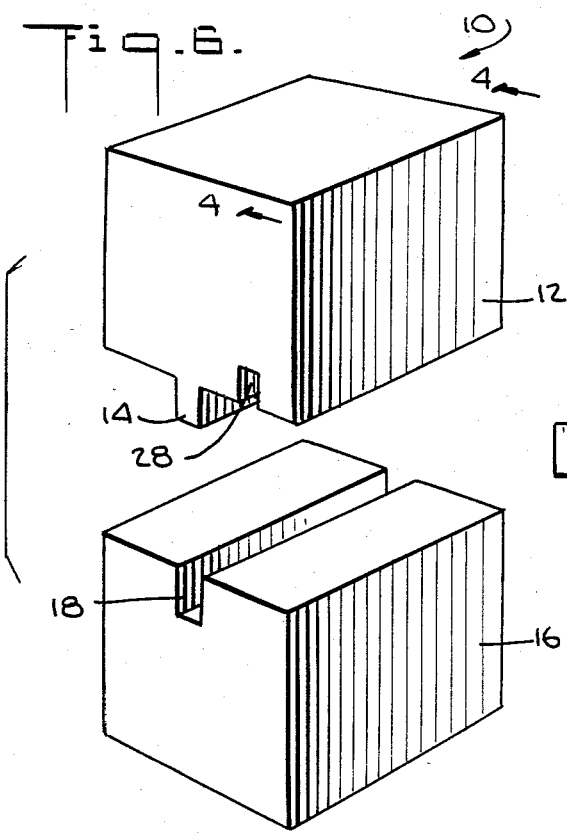
FIG. 6 is a perspective view of another embodiment of the hair volume measuring device of the present invention having a measuring slot therein.

The hair volume measuring device 10 of the present invention, by and large, is of a cube-shaped configuration comprising male and female members. It is made of metal, metal alloys or hard material such as plastic, porcelain, wood and glass by molding, casting and machining to desired precision using conventional technique of fabrication.

As can be seen in FIGS. 1 and 2, the hair volume measuring device 10 comprises: male members 12 having projection 14 extending therefrom; and female members 16 having a sample slot 18 to receive and hold hair sample 20 and to engage projection 14. The width of the generally rectangular shape projection 14 is slightly smaller than the width of the generally rectangular shape sample slot 18 for proper mating engagement of the same. In use, hair sample 20 having a length longer than the length of sample slot 18, is placed into sample slot 18. Male member 12 is placed on female member 16 so that projection 14 engages sample slot 18 in a mating relationship exerting force on hair sample 20 and compressing the sample to assume a generally rectangular configuration as can best be seen in FIG. 2. Portions of the hair sample on both sides of the device extend outward as shown in FIG. 3. To obtain the proper volume of the sample, defined by the space the sample occupies in sample slot 18, the portions of the hair sample projecting outward on both sides of the device are cut with a sharp instrument 22, such as a razor blade, as shown in FIG. 4. Subsequent to cutting, the hair sample 20 assumes the configuration 24 shown in FIG. 5. The length and width of this configuration is known from the predetermined dimensions of the sample slot, while the height of the same is measured by measuring the gap 26, shown in FIG. 2, between the surfaces of male member 12 and female member 16 of the device.

Figure 7:
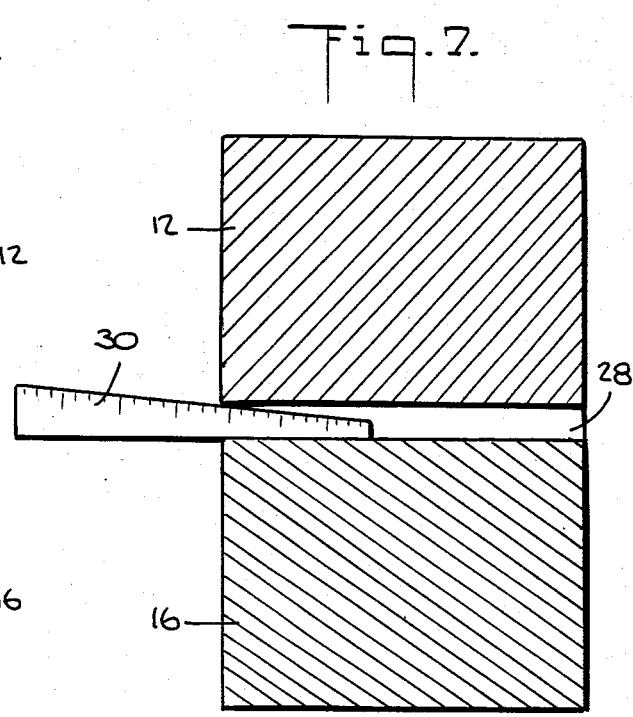
FIG. 7 is a cross sectional view of FIG. 6 along the line 4—4 and also showing a taper gauge inserted into the measuring slot.

FIGS. 6 and 7 show another embodiment of the hair volume measuring device of the present invention wherein like numbers denote like members and parts of the device shown in FIGS. 1-5. FIG. 6 is a perspective view of the embodiment in which, additionally, a measuring slot 28 is provided for measuring the height of a hair sample placed in sample slot 18 as previously described. Measuring device 30, such as a taper gauge, is inserted into measuring slot 28, as shown in FIG. 7, and the number on the measuring device that corresponds with the height of the sample is read.

Figure 8:
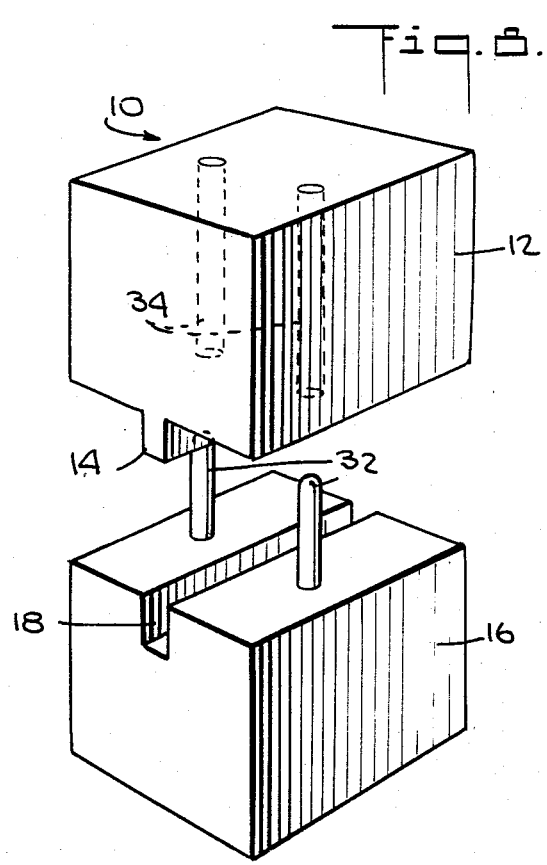
FIG. 8 is a perspective view of a further embodiment of the hair volume measuring device of the present invention having rods for insertion into corresponding holes.

FIG. 8 is a perspective view of a further embodiment of the present invention wherein like numbers denote like members and parts of the embodiments shown in FIGS. 1-7. The device of FIG. 8 is substantially the same as the device of FIGS. 1-5, however, it additionally contains a pair of rods 32 in female member 16 and corresponding receiving members or holes 34 in male member 12 for engagement thereof. Upon use for volume measurement, rods 32 are inserted into corresponding receiving members on holes 34 and male member 12 is pressed against female member 16. The engagement of said rods with said holes help to maintain parallel alignment of the respective surfaces of the male and female members of the device.

Figure 9:
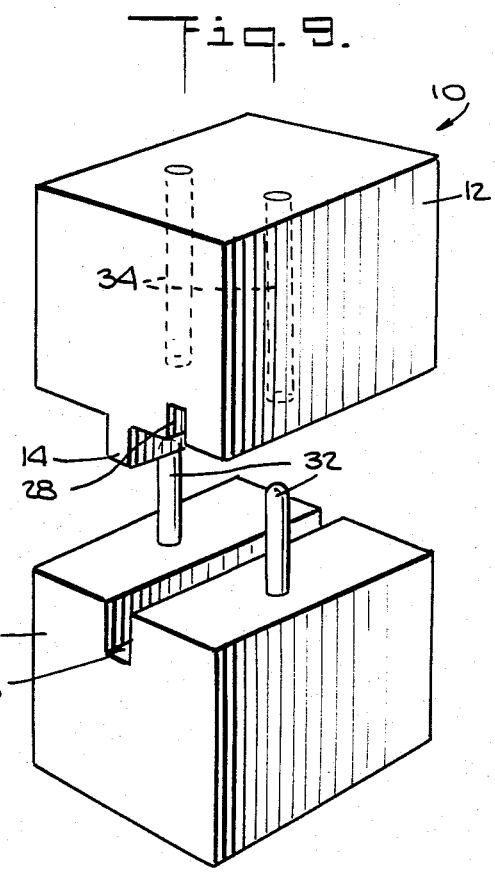
FIG. 9 is a perspective view of still another embodiment of the hair volume measuring device of the present invention having, in addition to rods and corresponding holes, a measuring slot therein.

FIG. 9 is a perspective view of still another embodiment of the hair volume measuring device of the present invention wherein like numbers denote like members and parts of the embodiments shown in FIGS. 1-8. The device of FIG. 9 is substantially the same as the device of FIG. 8, however, it additionally contains measuring slot 28 the function of which was previously explained in the description of FIGS. 6 and 7.

Measurement of hair volume is accomplished by placing a small sample of hair, having a length of at least as long as the length of the device, in the sample slot of the female member of the device and compressing the sample with the projection of the male member of the device. If sufficient hair has been placed in the sample slot, there will be a gap between the superimposed surfaces of the male and female members of the device. The distance between the surfaces, which is a measure of the thickness or height of the hair sample in the sample slot, is measured by a gauge such as an automotive feeler or taper gauge capable of measuring thickness in thousands of an inch. The gauge is inserted in the gap between the surfaces or in the measuring slot of the device especially provided for measuring purposes. Once the gauge reading has been recorded, the hair protruding from both sides of the sample slot is readily cut with a razor blade. The gauge reading is then used to determine the actual hair weight via the relationship of the least square line of best fit.

The examples that follow will further illustrate the utilization of the hair volume measuring device of the present invention.

EXAMPLE 1

The volumes of virgin hair samples, obtained from well mixed commercial sources, were measured with the device of the present invention having the following dimensions:

| | |
|---|---|
| slot depth: | 0.125" |
| slot width: | 0.045" |
| slot length: | 1.000" |
| compression element height: | 0.055" |
| compression element width: | 0.038" |

A feeler gauge was used to measure gap distance between male and female members of the block. Then the actual weights of the samples were taken on an analytical balance.

Results are shown in Table I.

TABLE I

Virgin Hair

| Gauge No. | Hair Weight, Mg. Actual | Calculated* |
|---|---|---|
| 4 | 44.3 | 40.1 |
| 4 | 37.9 | 40.1 |
| 4 | 37.7 | 40.1 |
| 4 | 40.5 | 40.1 |
| 4 | 40.7 | 40.1 |
| 5 | 39.3 | 41.8 |
| 5 | 44.1 | 41.8 |
| 7 | 45.5 | 45.1 |
| 7 | 42.0 | 45.1 |
| 7 | 46.8 | 45.1 |
| 8 | 46.0 | 46.6 |
| 8 | 49.0 | 46.6 |
| 8 | 45.5 | 46.6 |
| 9 | 45.6 | 47.9 |
| 9 | 47.3 | 47.9 |
| 10 | 44.8 | 49.2 |
| 11 | 53.5 | 50.4 |
| 11 | 49.7 | 50.4 |
| 12 | 50.9 | 51.5 |
| 17 | 53.5 | 55.5 |
| 18 | 55.3 | 56.0 |
| 23 | 55.7 | 57.1 |
| 24 | 58.8 | 57.0 |
| 25 | 57.3 | 56.8 |

*From the line of best fit
Weight = 32.0 + 2.21 (gauge) − .0487 (Gauge)$^2$
% Error: 3.8 ± 2.6%

EXAMPLE 2

The volumes of double bleached hair samples, obtained from well-mixed commercial sources, were measured with the hair volume measuring device of the present invention having the following dimensions:

| | |
|---|---|
| slot depth: | 0.125" |
| slot width: | 0.045" |
| slot length: | 1.000" |
| compression element height: | 0.055" |
| compression element width: | 0.038". |

A feeler gauge was used to measure gap distance between male and female members of the block. Subsequently, the actual weights of the samples were taken on an analytical balance. Results are shown in Table II.

TABLE II

Double Bleached Hair

| Gauge No. | Hair Weight, Mg. Actual | Calculated* |
|---|---|---|
| 5 | 44.1 | 41.8 |
| 6 | 46.6 | 43.5 |
| 7 | 44.6 | 45.1 |
| 9 | 49.9 | 47.9 |
| 10 | 49.7 | 49.2 |
| 11 | 51.2 | 49.2 |
| 12 | 52.5 | 51.5 |
| 15 | 54.9 | 54.2 |
| 23 | 58.8 | 57.1 |

*From the line of best fit
Weight = 32.0 + 2.21 (gauge) − .0487 (Gauge)$^2$
% Error: 3.2 ± 2.0%

EXAMPLE 3

The volumes of hair samples, taken from 20 different subjects were measured with the device of the present invention having the following dimensions:

| | |
|---|---|
| slot depth: | 0.150" |
| slot width: | 0.055" |
| slot length: | 0.500" |
| compression element height: | 0.058" |
| compression element width: | 0.043" |

A feeler gauge was used to measure gap distance between male and female members of the block. Subsequently, the actual weight of samples were taken on an analytical balance. Results, including percent error as weight difference between calculated and measured weights, are shown in Table III.

TABLE III

Caucasian Hair

| Feeler Gauge No. | Hair Weight[1] Found | Calculated | Error % |
|---|---|---|---|
| 5 | 35.0 | 36.4 | 3.8 |
| 5 | 36.1 | " | 0.8 |
| 5 | 34.6 | " | 4.9 |
| 5 | 38.0 | " | 4.4 |
| 6 | 39.0 | 37.1 | 5.1 |
| 6 | 36.4 | " | 1.9 |
| 10 | 40.1 | 40.0 | 0.3 |
| 10 | 40.6 | " | 1.5 |
| 12 | 40.0 | 41.4 | 3.4 |
| 14 | 45.6 | 42.9 | 6.3 |
| 14 | 42.3 | " | 1.4 |
| 14 | 42.6 | " | 0.7 |
| 15 | 43.8 | 43.6 | 0.5 |
| 15 | 42.1 | " | 3.4 |
| 15 | 43.4 | " | 0.5 |
| 16 | 45.3 | 44.3 | 2.3 |
| 16 | 41.7 | " | 5.9 |
| 16 | 44.5 | " | 0.5 |
| 16 | 43.4 | " | 2.0 |
| 17 | 48.3 | 45.0 | 7.3 |
| 18 | 47.6 | 45.8 | 3.9 |
| 28 | 51.5 | 52.9 | 2.6 |
| | | X = | 2.6 |

[1]From the relationship: Weight = .719 Gauge + 32.8

EXAMPLE 4

The volumes of hair samples were measured with the device of the present invention having the following dimensions:

| | |
|---|---|
| slot depth: | 0.100" |
| slot width: | 0.045" |
| slot length: | 1.000" |
| compression element height: | 0.055" |
| compression element width: | 0.038". |

A taper gauge was used to measure gap distance between male and female members of the block. The actual weight of samples were taken on an analytical balance. Results, including percent error as weight difference between calculated and measured weights, are shown in Table IV.

TABLE IV

Hair

| Taper Gauge No. | Hair Weight[1] Found | Calculated | Error % |
|---|---|---|---|
| 103 | 48.1 | 48.4 | 0.6 |
| 105 | 50.8 | 50.3 | 0.9 |
| 106 | 51.5 | 51.3 | 0.4 |
| 106 | 52.4 | 51.3 | 2.1 |
| 111 | 57.5 | 56.2 | 2.3 |
| 113 | 57.0 | 58.1 | 1.9 |
| 114 | 57.7 | 59.1 | 2.4 |

TABLE IV-continued

| Taper Gauge No. | Hair Hair Weight[1] | | Error % |
| --- | --- | --- | --- |
| | Found | Calculated | |
| 120 | 64.2 | 64.9 | 1.0 |
| 122 | 68.9 | 66.8 | 3.0 |
| 123 | 62.7 | 67.8 | 8.1 |
| 125 | 70.8 | 69.7 | 1.5 |
| 129 | 76.0 | 73.6 | 3.1 |
| 130 | 74.6 | 74.6 | 0.0 |
| | | X = | 0.9 |

[1]From line of best fit: Weight = 0.970 Gauge − 51.5

The above-shown data illustrate that the hair volume measuring device of the present invention is well suited for obtaining the weight of a small sample based on the measurement of the volume of the sample. It is to be noted that, in addition to measuring the gap between the male and female members of the block by the use of a feeler gauge or taper gauge, other methods or devices could be used as well, such as an optical micrometer. Also, in addition to utilizing the device in connection with hair sample measurements, the same may be utilized with other fibrous materials both natural and synthetic.

Upon obtaining the volume of a hair sample, its weight is calculated and the sample is placed into a vial, such as an optically clear ⅛ oz. screw capped bottle containing a copper solution of known or previously measured color intensity. Generally a non-volatile copper solution having $Cu^{++}$ ions stabilized with a complexing agent which complexes with the $Cu^{++}$, having a pH of about 9.0 to 9.5 is used in the practice of the present invention. The following formula is illustrative of formulations contemplated by the present invention.

| | |
| --- | --- |
| Sodium Tetraborate - $10H_2O$ (buffer agent) | 3.81 g |
| Copper Sulfate - $5H_2O$ | 3.90 g |
| Ethanolamine (complexing agent) | 3.99 g |
| Purified $H_2O$ qs to | 1000 ml |
| Final pH | 9.2 |

A complexing agent, such as ethanolamine, renders the solution stable for extended time periods. Illustrative of stability is the following data obtained on aging of the above-shown copper sulfate formula containing ethanolamine therein as the complexing agent.

| Time | Copper Sulfate/Ethanolamine % Stability | | |
| --- | --- | --- | --- |
| | Room Temp. | 40° C. | 50° C. |
| 1 year | 97.5% | 96.7% | 95.1% |
| 2 years | 95.1% | 93.4% | 90.9% |

The capped vial, containing the copper solution and hair sample is shaken, then heated for about a minute in boiling water to obtain a reaction between the copper reagent and negatively charged groups in the hair. The solution is then decanted into a cuvette and the color intensity measured. Color intensity measurement may be made by several methods including the following:

(a) Color Chart Method in which the color of the decanted solution is matched with color strips of varying intensities on a color chart. Corresponding to the color intensity of the strips are numbers denoting extent of hair damage.

(b) Color Tubes Method in which the color strips of the color chart method are replaced by sealed color tubes containing various concentrations of copper ions and the hair damage is estimated similarly as in (a).

(c) Glass Slides Method in which comparison of color intensity of the sample vial is made with colored glass slides.

(d) Electronic Optical Measurement methods instrumentally measuring color intensity such as, filter photometers and spectrophotometers.

Alternatively to measuring copper concentration by measuring color intensity, the same can be measured by impendance measurement, in which the concentration of copper in solution is measured via the inverse relationship of concentration to impendance.

Hair damage measurements were made utilizing the copper uptake method hereinbefore described and comparing the result obtained thereby with that of the Instron Stress/Strain Apparatus method. Hair damage measurement by the Instron Stress/Strain Apparatus is based on the force required to produce an elongation of 15% in hair length which force decreases with increasing hair damage.

EXAMPLE 5

Virgin hair samples were exposed to alkaline solution for varying length of time then washed free of alkali. Instron Stress/Strain and copper uptake measurements were made on the samples. Results are shown in Table V.

TABLE V

| Relative Force Required to Produce 15% Elongation | Increase in Copper Uptake, mg/g hair |
| --- | --- |
| 100 | 0.0 |
| 96.36 | 4.44 |
| 89.86 | 5.92 |
| 89.77 | 7.44 |
| 75.56 | 13.99 |
| 77.26 | 14.50 |

EXAMPLE 6

Virgin hair samples were treated with thioglycolate for varying time periods followed by treatment with bromate simulating a typical hair waving treatment. The hair samples were then washed free of residual materials. Instron Stress/Strain and copper uptake measurements were made on the samples. Results are shown in Table VI.

TABLE VI

| Relative Force Required to Produce a 15% Elongation | Increase in Copper Uptake, mg/g hair |
| --- | --- |
| 100.00 | 0.00 |
| 94.44 | 0.48 |
| 82.35 | 5.84 |
| 82.19 | 6.57 |
| 78.27 | 7.38 |
| 69.93 | 7.78 |
| 69.20 | 8.11 |

EXAMPLE 7

Virgin hair samples were treated weith the typical bleaching agents, hydrogen peroxide and potassium persulfate for varying lengths of time. Subsequent to treatment, the samples were washed free of residuals.

Instron Stress/Strain and copper uptake measurements were made on the samples. Results are shown in Table VII.

TABLE VII

| Relative Force Required to Produce 15% Elongation | Increase in Copper Uptake mg/g hair |
| --- | --- |
| 100.00 | 0.00 |
| 99.05 | 1.54 |
| 91.12 | 6.03 |
| 83.12 | 11.05 |

As can be ascertained from Tables V–VII, there exists a good correlation between results obtained by physical stress/strain measurement and that obtained by the copper uptake method of the present invention.

It will be understood that the preceding examples have been given for illustration purposes only and that this invention is not limited to the specific embodiments disclosed therein. It will also be readily apparent to those skilled in the art that many variations can be made of the hair volume measuring device as well as the method of measuring hair damage by the copper uptake method, within the limits set forth without departing from the spirit and scope of the invention.

What is claimed is:

1. A method of measuring hair damage based on copper reaction with active negative sites on hair comprising the steps of:
   (a) placing a known amount of hair into a sealed vial containing a water solution of a known amount of copper sulfate having $Cu^{++}$ ions that is stabilized with the complexing agent ethanolamine and buffered with sodium tetraborate, said solution having a pH of about 9.0 to 9.5;
   (b) reacting said solution with said hair by heating the vial; and
   (c) determining the copper uptake by the hair.

2. The method of claim 1 wherein the copper uptake determination is by impendance measurement of the copper solution decanted from the vial.

3. A method of measuring hair damage based on copper reaction with active negative sites on hair comprising the steps of:
   (a) placing a known amount of hair into a sealed optically clear vial containing a water solution of a known amount of copper sulfate having $Cu^{++}$ ions that is stabilized with the complexing agent ethanolamine and buffered with sodium tetraborate, said solution having a pH of about 9.0 to 9.5;
   (b) reacting said solution with said hair by heating the vial and decanting the residual solution for measuring its color intensity; and
   (c) determining the copper uptake by the hair by comparing the intensity of the decanted solution with color intensities of media which denote amounts of copper concentration.

4. The method of claim 3 wherein said media is a color chart.

5. The method of claim 3 wherein said media is color tubes containing various concentrations of copper.

6. The method of claim 3 wherein said media is colored glass slides.

7. The method of claim 3 wherein said comparing of color intensities of the copper solution and media having various color intensities is by electronic measurement.

8. The method of claim 7 wherein said electronic measurement is by a filter photometer.

9. The method of claim 7 wherein said electronic measurement is by a spectrophotometer.

* * * * *